US010729704B2

(12) United States Patent
Phillip et al.

(10) Patent No.: US 10,729,704 B2
(45) Date of Patent: *Aug. 4, 2020

(54) NUTRITIONAL SUPPLEMENTS FOR GROWTH ENHANCEMENT IN PRE-PUBERTAL ADOLESCENTS

(71) Applicant: NG Solutions LTD, Petach-Tikva (IL)

(72) Inventors: Moshe Phillip, Givataim (IL); Michal Yackobovitch-Gavan, Natania (IL); Raanan Shamir, Herzlia (IL); Hadassa Bymel, Haifa (IL)

(73) Assignee: NG Solutions LTD, Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 16/278,202

(22) Filed: Feb. 18, 2019

(65) Prior Publication Data

US 2019/0175620 A1 Jun. 13, 2019

Related U.S. Application Data

(63) Continuation of application No. 15/514,347, filed as application No. PCT/IL2015/050954 on Sep. 21, 2015, now Pat. No. 10,278,980.

(60) Provisional application No. 62/055,468, filed on Sep. 25, 2014.

(51) Int. Cl.
| | |
|---|---|
| *A61K 31/59* | (2006.01) |
| *A23L 33/00* | (2016.01) |
| *A23L 33/15* | (2016.01) |
| *A23L 33/16* | (2016.01) |
| *A23L 33/155* | (2016.01) |
| *A61K 9/14* | (2006.01) |
| *A61K 31/07* | (2006.01) |
| *A61K 31/375* | (2006.01) |
| *A61K 31/70* | (2006.01) |
| *A61K 33/00* | (2006.01) |
| *A61K 33/26* | (2006.01) |
| *A61K 33/30* | (2006.01) |
| *A61K 38/00* | (2006.01) |

(52) U.S. Cl.
CPC .............. *A61K 31/59* (2013.01); *A23L 33/15* (2016.08); *A23L 33/155* (2016.08); *A23L 33/16* (2016.08); *A23L 33/30* (2016.08); *A23L 33/40* (2016.08); *A61K 9/14* (2013.01); *A61K 31/07* (2013.01); *A61K 31/375* (2013.01); *A61K 31/70* (2013.01); *A61K 33/00* (2013.01); *A61K 33/26* (2013.01); *A61K 33/30* (2013.01); *A61K 38/00* (2013.01); *A23V 2002/00* (2013.01)

(58) Field of Classification Search
CPC .......... A61K 31/59; A61K 9/14; A61K 31/07; A61K 31/375; A61K 31/70; A61K 33/00; A61K 33/15; A61K 33/16; A61K 33/26; A61K 33/30; A61K 33/40; A61K 38/00; A23L 33/30; A23L 33/155; A23V 2002/00

See application file for complete search history.

(56) References Cited

U.S. PATENT DOCUMENTS

| | | | | |
|---|---|---|---|---|
| 5,719,134 | A | * | 2/1998 | Schmidl .................. A23L 33/40 514/168 |
| 10,342,827 | B2 | * | 7/2019 | Phillip .................. A61K 31/593 |
| 2006/0024408 | A1 | * | 2/2006 | Cicci ....................... A23L 33/15 426/72 |
| 2013/0017182 | A1 | | 1/2013 | Lukina |
| 2016/0022734 | A1 | | 1/2016 | Phillip et al. |
| 2017/0252359 | A1 | | 9/2017 | Phillip et al. |
| 2018/0140632 | A1 | | 5/2018 | Phillip et al. |

FOREIGN PATENT DOCUMENTS

| | | |
|---|---|---|
| WO | WO 03/035027 | 5/2003 |
| WO | WO 2016/046818 | 3/2016 |

OTHER PUBLICATIONS

Pediasure Growth Gain Protein Powder for Kids, Pediasure Product Description, 5 pages. (Year: 2014).*
Allen et al, Provision of Multiple Rather Than Two or Fewer Micronutrients More Effecttively Improve Growth and Other Outcomes in Micronutrient-Deficient Kids and Adults, Journal of Nutrition, 139(5): 1022-1030 (Year: 2009).*
Communication Pursuant to Article 94(3) EPC dated Jul. 11, 2019 From the European Patent Office Re. Application No. 15844014.9. (8 Pages).
International Preliminary Report on Patentability dated Mar. 28, 2017 From the International Bureau of WIPO Re. Application No. PCT/IL2015/050954. (7 Pages).
International Search Report and the Written Opinion dated Jan. 12, 2016 From the International Searching Authority Re. Application No. PCT/IL2015/050954. (10 Pages).
Notice of Allowance dated Dec. 26, 2018 From the US Patent and Trademark Office Re. U.S. Appl. No. 15/514,347. (5 pages).
Official Action dated May 24, 2018 From the US Patent and Trademark Office Re. U.S. Appl. No. 15/514,347. (13 pages).
Official Action dated Oct. 25, 2018 From the US Patent and Trademark Office Re. U.S. Appl. No. 15/514,347. (10 pages).
Restriction Official Action dated Feb. 28, 2018 From the US Patent and Trademark Office Re. U.S. Appl. No. 15/514,347. (8 pages).
Supplementary European Search Report and the European Search Opinion dated Feb. 27, 2018 From the European Patent Office Re. Application No. 15844014.9. (14 Pages).
Allen et al. "Provision of Multiple Rather Than Two or Fewer Micronuctrients More Effectively Improves Growth and Other Outcomes in Micronutrient-Deficient Children and Adults", The Journal of Nutrition, XP055419832, 139(5): 1022-1030, Published Online Mar. 25, 2009. Abstract, p. 1022-1023, col. 2.

(Continued)

*Primary Examiner* — Carlos A Azpuru

(57) ABSTRACT

Provided are nutritional supplements designed for enhancing the growth, particularly the linear growth, of pre-pubertal children with a stature measure short compared to the norm. The nutritional composition comprises an energy source, and a combination of micronutrients, and is adapted separately for the nutritional needs of male or female adolescents.

10 Claims, No Drawings

(56) References Cited

OTHER PUBLICATIONS

Corfranlait "GNPD—High Protein Milk Formula", Nestl? Switzerland, XP055451725, Product Information, p. 1-2, Dec. 2007. p. 1.
Nestle "GNPD—Children Milk Powder", Nestl? Switzerland, XP055451677, Product Informaiton, p. 1-3, Aug. 2014. p. 1-2.
PediaSure "PediaSure® Grow & Gain Protein Powder for Kids", Pedia Sure®, Product Description, 5 P., Jul. 1, 2014.
PediaSure "PediaSure® Grow & Gain", Product Descriptions, Abbot Laboratories, 3 P, 2018.
Rivera et al. "The Effect of Micronutrient Deficiencies on Child Growth: A Review of Results From Community-Based Supplementation Trials", The Journal of Nutrition, XP055451500, 133(11/Suppl.2): 4010S-4020S, Nov. 2003. Abstract.

\* cited by examiner

NUTRITIONAL SUPPLEMENTS FOR GROWTH ENHANCEMENT IN PRE-PUBERTAL ADOLESCENTS

RELATED APPLICATIONS

This application is a continuation of U.S. patent application Ser. No. 15/514,347 filed on Mar. 24, 2017 which is a National Phase of PCT Patent Application No. PCT/IL2015/050954 filed on Sep. 21, 2015 which claims benefit of priority of U.S. Provisional Patent Application No. 62/055,468 filed on Sep. 25, 2014.

FIELD AND BACKGROUND OF THE INVENTION

The present invention relates to the field of nutritional supplements. In particular, the present invention relates to a nutritional supplement comprising an energy source together with standardized amounts of micronutrients effective in enhancing the growth of short and lean pre-pubertal adolescents.

Adequate nutrition is essential for normal growth and development. During the lifetime of an individual, the growth during adolescence is faster than any other time period except during the first year of life. The phenomenal growth that occurs in adolescence, the pubertal spurt, creates increased demands for energy and nutrients (Jacob & Nair, 2012, January; 79 Suppl 1:S84-91).

Thus, nutrition plays an important role in pubertal growth. When a child or adolescent becomes malnourished, growth, including pubertal growth, will be attenuated. Adolescence can be the second opportunity to catch up growth if environmental conditions, especially in terms of nutrient intake are favorable. Therefore, adolescence is considered to be a nutritionally critical period of life (Jacob & Nair, ibid).

The nutritional needs of males and females are similar in childhood. However, after the onset of the pubertal growth spurt, there is a divergence. The reasons for this difference in nutrient requirements include earlier maturation of females and variations in physiological needs for some nutrients like protein, iron and B-vitamins. In addition to the weight and height differences, boys gain more muscle mass than fat compared to girls. Also, boys experience increased linear growth to produce a heavier skeleton and develop greater red blood cell mass than girls. Girls, on the other hand, accumulate more fat than muscle tissues. Overall, these differences in physiology have important implications for nutritional needs of male and female adolescence.

Growth is the fundamental physiologic process that characterizes childhood, and adequate nutrition is crucial for normal growth. In a rapidly growing child, there is an increased need for "building material" for the newly synthesized tissues.

Height as a growth parameter is measured as a linear stature at a single point in time compared to expected norms. The norms are typically provided by the general population as depicted in growth charts consisting of a series of percentile curves that illustrate the distribution of selected body measurements in children (for example, the charts of the Centers for Disease Control and Prevention (CDC)). Growth can be worrisome along two variables: height (short stature) and velocity (growth failure).

Protein-energy malnutrition (PEM) is the most important nutritional disease in developing countries because of its high prevalence and its connection with increased morbidity and mortality in all age groups as well as impaired physical growth and mental performance. Associated deleterious effects on physical and mental growth and maturation have been demonstrated in experimental animals and they seem to occur in humans. Nevertheless, one cannot dissociate completely the nutritional factors from other environmental conditions, or to ascertain irreversibility of the consequences of malnutrition.

In developed countries, where plenty of variable food is available, fat and carbohydrate intake of short small for gestational age (SGA) pre-pubertal children was found to be significantly lower compared to the recommended daily intake or dietary reference intake (DRI) for age-matched children (Boonstra et al, 2006, Horm Res, 65:23-30). In addition, the caloric intake of children with idiopathic short stature was positively correlated with growth velocity both before growth hormone (GH) treatment and during the first year of GH treatment (Zadik et al, 2005, Pediatrics 2005; 116(1): 68-72).

The factors that influence energy needs of adolescents are activity level, basal metabolic rate and increased requirements to support pubertal growth and development. Adolescent males have higher caloric requirements since they experience greater increase in weight, height and lean body mass than females.

The protein Recommended Dietary Allowance (RDA) for adolescents is 0.8 g/kg body weight, with a large acceptable range between 10%-30% of the total daily energy intake (DRI, 2005). Adequate protein consumption is essential to meet the growth requirements and maintenance of existing lean body mass and accrual of additional lean body mass during the adolescent growth spurt (Beckett et al, 1997; European Journal of Clinical Nutrition 2000; 54(Suppl. 2): S52-9). When protein intake is consistently inadequate, reduction in linear growth, delay in sexual maturation and reduced accumulation of lean body mass may be seen (Torum & Chew, ibid).

Micronutrients are nutrients required only in minute amounts by the human body, that nevertheless play a critical role in the normal growth and development of the body. Deficiencies in micronutrients can lead to a breakdown in numerous bodily functions and result in a plethora of mild to severe disorders. Since the human body is not capable of synthesizing most of the essential micronutrients, the only way to obtain them is through dietary food sources or through supplementation.

The principal micronutrients fall into two categories—vitamins and minerals. Vitamins are essential micronutrients that the body is not capable of synthesizing in sufficient quantities for its growth and maintenance and have to be derived from dietary food sources. However, most vitamins are present only in minute quantities in the foods that we ingest and their bioavailability depends on the food source. There are thirteen essential vitamins of which four, A, D, E, and K are fat soluble and nine, B1, B2, B3, B6, B12, pantothenic acid, biotin, folic acid, and C are water soluble. The fat soluble vitamins are capable of being retained in the body while the water soluble vitamins are excreted from the body.

Minerals which form the second category of micronutrients are inorganic in nature and can be broken down into two sub-categories: macrominerals such as calcium (Ca), phosphorous (P), sodium (Na), potassium (K), magnesium (Mg), and chloride (Cl) and trace minerals such as iron (Fe), zinc (Zn), iodine (Io), selenium (Se), copper (Cu), manganese (Mn), fluoride (fl), chromium (Cr) and molybdenum (Mo). Just as with the essential vitamins, these mineral micronutrients are essential for bodily functions and cannot be synthesized by the body. Therefore, it is necessary to have an adequate intake of these mineral micronutrients from food sources or through supplementation.

Several micronutrients including zinc, iron and vitamin A have been shown to play a critical role in normal growth. The most conclusive evidence to date linking the intake of a specific micronutrient to child growth is for zinc, though the mechanisms by which zinc deficiency impairs growth has not been elucidated. Iron deficiency is associated with anemia and impaired physical growth, but iron supplement alone had no significant effect on child growth (e.g. Ramakrishnan U et al., 2004; Journal of Nutrition; 134: 2592-602). Several observational studies reported significant correlations between vitamin A status and stunting (Fawzi W W et al., 1997, Epidemiology; 8: 402-7; Kurugol Z et al., 2000, Paediatrics Perinatal Epidemiology 2000; 14: 64-9). However, a later Meta analysis by Ramakrishnan et al. (2004, ibid) concluded that vitamin A supplementation interventions had no significant effect on growth.

Most of the studies which explored the role of specific nutrients in growth and the effect of supplements enriched with these nutrients have focused on malnourished children populations in developing countries.

The effect of a commercially available nutritional composition (PediaSure®) on weight-for-height measurements have been examined in children age 3-5 years with picky-eater behaviors in the Philippines and Taiwan. The supplement is designed to provide complete balanced nutrition for children 1-6 years. However any influence of any kind of combinations of micronutrients on linear growth in short stature adolescents has not been evaluated and no such nutritional composition is commercially available.

There is an unmet need for, and it would be highly advantageous to have a nutritional supplement specifically designed to enhance the linear growth of pre-pubertal adolescents who are significantly shorter and leaner than the norm and that also affects the pubertal growth spurt of these adolescents.

SUMMARY OF THE INVENTION

The present invention provides nutritional supplements specifically designed to improve the growth, particularly the linear growth, of pre-pubertal male and female adolescents who are significantly short compared to the norm, including healthy pre-pubertal adolescents. The nutritional supplements of the invention provide at least one measure of improved growth selected from growth rate enhancement; maintenance of normal growth rate; increasing growth spurt; elevating the final stature of a human subject and positively affecting the pubertal process. The present invention further provides nutritional supplements that differentiate between males and females according to their needs. The nutritional supplements of the invention are balanced, providing a full complement of nutrients for adolescents according to their gender. The nutritional supplements of the invention fulfill an unmet need for tailored supplements according to age and gender.

The present invention is based in part on the unexpected discovery that a nutritional supplement comprising an energy source and a particular combination of macro- and micro-nutrients is significantly effective in enhancing the linear growth of pre-pubertal adolescents; enhancing pubertal growth spurt; and accelerating pubertal onset in children that are below the 10$^{th}$ percentile in terms of height and weight when intervention is initiated.

Without wishing to be bound by any particular theory or mechanism of action, the efficacy of the nutritional supplement of the invention may be attributed to the specific composition and ratios of the micronutrients within the nutritional supplement formula resulting in optimal absorption and synergistic activity. According to the principles of the present invention the micronutrients, together with a highly balanced energy source including low fat and high protein content provide for the growth stimulation.

Moreover, the present invention discloses for the first time that nutritional supplements tailored according to the gender of the adolescent, particularly in terms of iron and vitamin content as well as of total calories and content of macronutrients, including protein and fat, provides for the improved growth and pubertal process of short for age adolescents.

According to one aspect, the present invention provides a nutritional supplement in powder form having per 100 g of powder a total caloric content of from about 400 kcal to about 600 kcal, said nutritional supplement comprising per 100 g powder a micronutrient combination comprising calcium in an amount of from about 250 mg to about 650 mg; vitamin C in an amount of from about 15 mg to about 50 mg; zinc in an amount of from about 5.0 mg to about 10 mg; iron in an amount of from 4.6 mg to 10 mg; vitamin A in an amount of from 350 µg to about 400 µg; and vitamin D in an amount of from about 2 µg to about 10 µg.

According to some embodiments, 40% to 70% of the total caloric content is carbohydrates.

According to some embodiments, 10% to 40% of the total caloric content is fat.

According to some embodiments, 10% to 40% of the total caloric content is proteins. According to some embodiments, the amino acids provided by the nutritional supplement are present in the form of the proteins present in the composition, and no free amino acid is added to the composition. According to some embodiments the nutritional supplement does not contain arginine as a free amino acid.

According to some embodiments, 40% to 70% of the total caloric content is carbohydrates; 10% to 40% of the total caloric content is fat; and 10% to 40% of the total caloric content is proteins.

According to some embodiments, the carbohydrate content is from 40 to 70 g per 100 g powder, the total fat content is below 20 g/100 g powder, and the total protein content is above 20 g/100 g powder. According to certain exemplary embodiments, the total protein content is from about 20 g/100 g powder to about 40 g/100 g powder. According to additional exemplary embodiments, the total fat content is from about 10 g/100 g powder to about 20 g/100 g powder.

According to some embodiments, the nutritional supplement comprises out of the total protein content from about 600 mg to about 1250 mg arginine per 100 g powder.

According to some embodiments, the nutritional supplement comprises out of the total protein content from about 2 g to 4 g lysine per 100 g powder.

According to some embodiments, the nutritional supplement comprises out of the total protein content from about 0.7 g to about 1.3 g tyrosine and/or leucine in an amount of from about 2.5 g to about 4.5 g per 100 g powder.

According to some embodiments, the nutritional supplement is formulated in a unit dosage form selected from the group consisting of a sachet, a tablet and a pre-measured dosage within a container.

According to some embodiments, the nutritional supplement is for a pre-pubertal male adolescent and comprises iron in an amount below 5 mg per 100 g powder. According to certain embodiments, the male adolescent age is more than 11 years. According to other embodiments, the male adolescent age is more than 13 years. According to certain embodiments, the nutritional composition is formulated in a unit dosage form. According to certain exemplary embodiments, the unit dosage form contains the recommended total powder amount per day. According some exemplary embodiments, the recommended dosage form for males contains about 130 g.

According to some embodiments, the nutritional supplement is for a pre-pubertal female adolescent and comprises iron in an amount of above 5 mg per 100 g powder According to certain embodiments, the female adolescent age is more than 10 years. According to other embodiments, the female adolescent age is more than 12 years. According to certain embodiments, the nutritional composition is formulated in a unit dosage form. According to certain exemplary embodiments, the unit dosage form contains the recommended total powder amount per day. According to some exemplary embodiments, the recommended dosage form for females contains 112 g.

The nutritional supplement of the invention can be formulated in any suitable form as is known to a person skilled in the art. According to some embodiments, the content of the single dosage form is for dilution in water or another beverage. According to certain embodiments, the nutritional supplement is in a powder form for dilution with water or other beverage before use.

According to some embodiments, the nutritional supplement is formulated as a ready-to-use supplement. According to certain embodiments, the ready-to-use supplement is in a form selected from the group consisting of a liquid, a paste, a pudding and a solid bar.

According to some embodiments, the nutritional supplement is for enhancing the linear growth of pre-pubertal human adolescent subject.

According to another aspect, the present invention provides a method for improving the growth of a pre-pubertal human adolescent, comprising administering a nutritional supplement to a pre-pubertal human adolescent having a short stature compared to the norm, wherein the nutritional supplement has per 100 g powder a total caloric content of from about 400 kcal to about 600 kcal comprising per 100 g powder a micronutrient combination comprising calcium in an amount of from about 250 mg to about 650 mg; vitamin C in an amount of from about 15 mg to about 50 mg; zinc in an amount of from about 5.0 mg to about 10 mg; iron in an amount of from about 4.6 mg to about 10 mg; vitamin A in an amount of from about 350 µg to about 400 µg; and vitamin D in an amount of from about 2 µg to about 10 µg, thereby improving the growth of the pre-pubertal human adolescent.

According to some embodiments, the pre-pubertal human adolescent is a male and the nutritional supplement comprises iron at an amount of below 5 mg per 100 g powder. According to these embodiments, the nutritional supplement is administered at an amount of 130 g/day.

According to some embodiments, the pre-pubertal human male is more than 11 years old. According to additional embodiments, the pre-pubertal adolescent male is more than 13 years old.

According to some embodiments, the pre-pubertal human adolescent is a female and the nutritional supplement comprises iron at an amount of above 5 mg per 100 g powder. According to these embodiments, the nutritional supplement is administered at an amount of 112 g/day.

According to some embodiments, the pre-pubertal human female is more than 10 years old. According to additional embodiments, the pre-pubertal human female is more than 12 years old.

According to some embodiments, the pre-pubertal adolescent height is below the $10^{th}$ percentile. According to additional embodiments, the subject weight is also below the $10^{th}$ percentile.

According to some embodiments, the pre-pubertal human adolescent is healthy.

According to some embodiments, the pre-pubertal human adolescent has normal levels of growth hormone.

According to some embodiments, the method results in enhancing the growth rate of the pre-pubertal adolescent.

According to some embodiments, the growth rate is enhanced by additional 0.5-3.0 cm per year relative to the expected growth rate. According to some embodiments, the method results in elevating the final stature measure of said subject relative to the expected measure. According to certain embodiments, the final stature measure is elevated by 0.5 cm to 5 cm.

According to some embodiments, the method is for maintaining the growth rate of the pre-pubertal adolescent.

According to some embodiment, the method results in accelerating pubertal onset and stimulate pubertal spurt.

According to some embodiments, the nutritional supplement comprises per 100 g powder a total caloric content of 440 kcal, comprising per 100 g powder a micronutrient combination comprising calcium in an amount of about 415 mg; vitamin C in an amount of about 23 mg; zinc in an amount of about 6.1 mg; iron in an amount about of about 4.6 mg; vitamin A in an amount of about 385 µg; and vitamin D in an amount of 2.3 µg, said nutritional supplement is for male adolescents. According to these embodiments, the nutritional supplement comprises carbohydrate content of about 49 g/100 g powder; total fat content of about 14.7 g/100 g powder; and protein content of about 27.7 g/100 g powder.

According to some embodiments, the nutritional supplement comprises per 100 g powder a total caloric content of 440 kcal, comprising per 100 g powder a micronutrient combination comprising calcium in an amount of about 446 mg; vitamin C in an amount of about 27 mg; zinc in an amount of about 7.1 mg; iron in an amount of about 6.2 mg; vitamin A in an amount of about 357 µg; and vitamin D in an amount of 2.7 µg, said nutritional supplement is for female adolescents. According to these embodiments, the nutritional supplement comprises carbohydrate content of about 49 g/100 g powder; total fat content of about 14.7 g/100 g powder; and protein content of about 27.7 g/100 g powder.

The vitamins, minerals, proteins, fat and carbohydrates included in the nutritional supplements of the invention are used in any suitable form for producing the nutritional powder or ready-to-use formula of the invention. According to certain embodiments, the vitamin and minerals are provided in a readily bio-available form. According to certain exemplary embodiments, the vitamin and minerals are provided in their most bio-available form.

According to certain embodiments, the nutritional supplement of the invention is administered to male adolescent at an amount of at least 2.5 g/kg body weight/day. According to some embodiments, the body weight (BW) is the weight measured when intervention is initiated. According to other embodiments, the supplement is administered at an amount of between 2.5 to 5.0 g per kg BW/day.

According to certain embodiments, the nutritional supplement of the invention is administered to female adolescent at an amount of at least 3.0 g/kg BW/day. According to some embodiments, the body weight is the weight measured when intervention was initiated. According to other embodiments, the supplement is administered at an amount of between 2.2 to 5.0 g per kg BW/day. There is no significance to the number of portions of the nutritional supplement consumed as long as the recommended total effective amount of about 130 g/day for male and about 112 g/day for females is consumed. According to certain exemplary embodiments, the total recommended amount of the nutritional supplement is administered in two portions daily.

It is to be understood that any combination of each of the aspects and the embodiments disclosed herein is explicitly encompassed within the disclosure of the present invention.

Other objects, features and advantages of the present invention will become clear from the following description.

DESCRIPTION OF SPECIFIC EMBODIMENTS OF THE INVENTION

The present invention provides nutritional supplement tailored to meet the need to improve the growth, particularly the linear growth of pre-pubertal adolescents with short stature and typically lean body structure.

The nutritional composition of the present invention is so designed as to provide adequate amounts and combination of micronutrients and macronutrient along with optimized energy content. Moreover, the composition of the various ingredients within the nutritional supplement has been planned to ensure optimal absorption of each and every element in its bio-active form providing maximal activity within the human body.

As used herein the terms "improved growth" or "improving the growth" relate to an enhancement in growth rate; maintenance of normal growth rate and elevating the final stature measure of a human subject. The term "expected growth rate" is based on growth charts for example CDC growth charts for the weight for age percentile.

The term "pre-pubertal adolescents" refers to boys above 11 or 13 years old, and girls that are above 10 or 12 years old that are at tanner stage 1. Tanner scale (or stages) is a scale of physical development in children. Tanner stage 1 is characterized, inter alia, by testicular volume of less than 4 ml for boys, and no glandular tissue for girls.

The term "accelerating pubertal onset" refers to correlating the pubertal onset of the adolescent subject to his developmental stage. Short and/or lean to age adolescent tend to have a delayed pubertal onset. By "accelerating pubertal onset" it means eliminating or reducing this delay.

The term "fat" is used as a generic term for lipids oils and the like that are edible, said term being entirely in the common knowledge of a person of skill in the art.

The terms "micronutrient" or "micronutrients" are used herein in their broadest scope as is known to a person skilled in the art. Micronutrients are nutrients required by humans and other organisms throughout life in small quantities to orchestrate a range of physiological functions.

As used herein, the term "about" refers to the designated measure ±10%. For example, about 300 kcal should mean from 270 to 330 kcal.

According to one aspect, the present invention provides a nutritional supplement in powder form having per 100 g of powder a total caloric content of from about 400 kcal to about 600 kcal, said nutritional supplement comprising per 100 g powder a micronutrient combination comprising calcium in an amount of from about 250 mg to about 650 mg; vitamin C in an amount of from about 15 mg to about 50 mg; zinc in an amount of from about 5.0 mg to about 10 mg; iron in an amount of from about 4.6 mg to 10 mg; vitamin A in an amount of from 351 µg to 400 µg; and vitamin D in an amount of from about 2 µg to about 10 µg.

According to additional aspect, the present invention provides a nutritional supplement in a powder form having per 100 g powder a total caloric content of from about 400 kcal to about 600 kcal comprising per 100 g powder a micronutrient combination comprising calcium in an amount of from about 250 mg to about 650 mg; vitamin C in an amount of from about 15 mg to about 50 mg; zinc in an amount of from about 5.0 mg to about 10 mg; iron in an amount of from about 4.6 mg to 10 mg; vitamin A in an amount of from 350 µg to about 400 µg; and vitamin D in an amount of from about 2 µg to about 10 µg.

According to some embodiments, the nutritional supplements further comprises per 100 g powder protein in an amount of from about 25 g to about 30 g.

According to some embodiments, the nutritional supplement further comprises per 100 g powder nutritional fibers in an amount of from about 1.3 g to about 2.1 g.

According to additional embodiments, the nutritional composition further comprises per 100 g powder sodium in an amount of from about 280 mg to about 400 mg and/or potassium in an amount of from about 400 mg to about 750 mg and/or phosphorus in an amount of from about 300 mg to about 550 mg and any combination thereof.

Several micronutrients, including zinc, iron and vitamin A have been previously reported to play a role in normal growth of the human body.

Zinc is an essential mineral that is naturally present in some foods. Several hundred zinc-containing nucleoproteins are involved in gene expression of multiple proteins, many of which are important for growth. Moreover, zinc deficiency reduces the production of insulin-like growth factor-1 (IGF-1) and may decrease cellular IGF responsiveness (Cole C R and Lifshitz E, 2008, Pediatric Endocrinology reviews, 5(4): 889-96). Multiple studies have been carried out to assess the effect of zinc supplementation on children's growth. A mete-analyses of 33 randomized controlled intervention trials revealed that zinc supplementation produced significant positive responses in height and in weight increments (Brown K H et al., 2002. Am J Clin Nutr 75:1062-71). In children with idiopathic short stature with normal serum zinc levels, zinc supplementation increased basal IGF-I, IGFBP-3, alkaline phosphatase and osteocalcin without changing growth hormone response to clonidine. Despite improvement in the above parameters, zinc supplementation did not significantly changed height or weight-SDS during 6-12 months follow-up period. Zinc supplementation did not affect sensitivity to exogenous growth hormone as tested by IGF-I and IGFBP-3 generation test (Imamoglu S et al., 2005. J Pediatr Endocrinol Metab 18(1): 69-74).

Several observational studies have documented a relationship between iron-deficiency anemia and impaired physical growth. The proposed mechanisms through which iron deficiency may impair growth include its effects on immunity, appetite, thermogenesis and thyroid hormone metabolism (for example, Lawless J W et al., 1994. J Nutr. 124(5):645-54.). A Meta analysis by Ramakrishnan et al. (2004, ibid) found that although iron interventions resulted in a significant increase in hemoglobin concentrations with an effect size of 1.49 (95% CI: 0.46, 2.51), there was no significant effect of iron supplementation intervention on child growth. Similar results and conclusions were made by a later systematic review of randomized controlled trials by Sachdev H P S et al., (2006, Public health Nutrition 9(7):904-20) where the pooled estimates did not document a statistical significant positive effect of iron supplementation on any anthropometric variable (weight for age, weight for height, height for age). It is important to note that most of the studies included in the Meta analysis of Ramakrishnan et al. (2004, ibid) and the systematic review of Sachdev et al. (2006, ibid) were from developing countries, where food supply is limited. In such conditions, even improvement in the child's appetite may not translate into increased energy intake, and therefore enhanced linear growth. Beckett et al. documented a significant increase in physical growth in undernourished Indonesian children with combination of energy and iron supplementation, but this finding needs further validation (Beckett C et al. 2000. Eur J Clin Nutr. 54 Suppl 2:S52-59).

Significant correlations between vitamin A status and stunting have been found in several observational studies (Fawzi et al., 1997, ibid; Fuchs G J et al. 1994. Am J Clin Nutr 60: 293-298; Kurugol et al, 2000, ibid). The results from randomized controlled trials (RCTs), however, are contradictory (Ramakrishnan et al. 2004, ibid). In a review by Bhandari et al., the authors concluded that routine vitamin A supplementation has little or no impact on linear growth, and that more research is needed to allow any conclusion on the impact of vitamin A in children with deficiency in this vitamin (Bhandari N et al., 2001. Br J Nutr 85(suppl 2): S131-S137). A later Meta analysis by Ramakrishnan et al (2004, ibid) concluded that vitamin A supplementation interventions had no significant effect on growth.

The particular combination of micronutrients provided in a nutritional composition is of significance in exerting each of the micronutrient activity. Few RCTs examined the effect of zinc-iron supplementation on linear growth of stunted children. Perrone et al. evaluated the effect of one year supplementation of iron plus zinc, zinc alone and placebo on growth (Perrone L et al., 1999. J Trace Elem Med Biol 1999; 13(1-2):51-56). Before supplementation, serum and erythrocyte ferritin and hair zinc contents were significantly lower in the short study group compared to age-matched control subjects. Iron plus zinc supplementation caused an improvement in growth rate in all subjects. In the zinc-supplemented group, only children whose ferritin levels were higher than 20 ng/L before provided with supplements showed a similar improvement of growth rate. Similar benefit to the combination of zinc and iron supplementation was found in a later large double-blind intervention study by Fahmida et al. (Fahmida U et al., 2007. Asia Pac J Clin Nutr 2007; 16(2): 301-309). This study involved 800 infants 3-6 month from west Tenggara. Syrup consists of zinc alone, zinc+iron, zinc+iron+vitamin A or placebo, were given daily for six months. The results showed a positive effect on linear growth among initially stunted infants in the zinc+iron, zinc+iron+vitamin A groups who grew 1.1-1.5 cm longer then placebo. In the zinc-alone group, mean height for age Z-score decreased to a greater extent than placebo. The authors attribute this finding to the low iron status of the subjects, and comment that zinc supplementation would have positive effect on growth if the low iron status is also corrected (Fahmida et al, 2007, ibid). On the other hand, in the study of Rosado et al. (1997) no differences in linear growth were observed between Mexican children supplemented with zinc and iron as compared to children receiving placebo for one year (Rosado J L et al., 1997. Am J Clin Nut 65:13-19). The investigators attributed the lack of impact to concurrent deficiencies of other micronutrients. In a later study of Rosado et al (Rosado J L et al., 1999. J of Nut 129:531S-533S), when mixture of micronutrients was given as a supplement to children over a period of one year, a small significant impact on linear growth was found (effect size 0.14 SD units), and a greater benefit was observed in children receiving the supplement that belonged to the low and medium socio-economic status.

In addition to supplying a combination of micronutrients, the composition of the present invention further supplies energy. Without wishing to be bound by a specific theory or mechanism of action, this combination may provide for the significant effect of the nutritional supplement of the invention on the linear growth of pre-pubertal children.

According to certain embodiments, 40% to 70% of the total caloric content of the supplement is carbohydrates. According to other embodiments, 10% to 40% of the total caloric content is fat. According to yet additional embodiments, 10% to 40% of the total caloric content is proteins. Each possibility represents a separate embodiment of the invention.

According to certain exemplary embodiments, the carbohydrate component of the nutritional supplement comprises from 38% to 52% of the total caloric content of the supplement. According to yet other exemplary embodiments, the carbohydrate component of the nutritional supplement comprises about 43% of the total caloric content of the supplement. According to yet other exemplary embodiments, the carbohydrate component of the nutritional supplement comprises about 46% of the total caloric content of the supplement.

Any carbohydrate conventionally used in nutritional compositions is useful in the composition of the supplement of this invention. According to certain exemplary embodiments, carbohydrate component is selected from the group consisting of, but not limited to sucrose, modified starch, nutritional fibers and combinations thereof.

According to additional exemplary embodiments, the fat component of the nutritional supplement comprises from 20% to 35% of the total caloric content of the supplement. According to yet other exemplary embodiments, the fat component of the nutritional supplement comprises about 30% of the total caloric content of the supplement.

Adequate fat intake is important as a source of energy and essential fatty acids and as a carrier of fat soluble vitamins. Suitable fat for use according to the teachings of the present invention include any of the conventional saturated and unsaturated fatty acids, glycerides and other nutritionally acceptable fat sources known in the art, such fat sources include animal oils, fish oils, vegetable oils and synthetic lipids. According to certain exemplary embodiments, the lipid component of the nutritional supplement consists essentially of canola oil.

According to further exemplary embodiments, the protein component of the nutritional supplement comprises from 20% to 32% of the total caloric content of the supplement. According to yet other exemplary embodiments, the protein component of the nutritional supplement comprises about 25% of the total caloric content of the supplement.

According to certain exemplary embodiments the protein component is selected from the group consisting of, but not limited to, whey protein, low fat milk powder and combination thereof.

The nutritional compositions of the invention may provide minimal, partial, or total nutritional support. In preferred exemplary embodiments, the supplement is administered in conjunction with a food or other nutritional composition. In these embodiments, the compositions can either be intermixed with the food or other nutritional compositions prior to ingestion by the subject or can be administered to the subject either before or after ingestion of the food or other nutritional composition.

The supplement may, but need not, be nutritionally complete. The skilled Artisan will recognize "nutritionally complete" to vary depending on a number of factors including, but not limited to, age, clinical condition, and dietary intake of the subject to whom the term is being applied. In general, "nutritionally complete" means that the nutritional supplement of the present invention provides adequate amounts of all carbohydrates, lipids, essential fatty acids, proteins, essential amino acids, conditionally essential amino acids, vitamins, minerals, and energy required for normal growth. As applied to nutrients, the term "essential" refers to any nutrient which cannot be synthesized by the body in amounts sufficient for normal growth and to maintain health and which therefore must be supplied by the diet. The term "conditionally essential" as applied to nutrients means that the nutrient must be supplied by the diet under conditions when adequate amounts of the precursor compound is unavailable to the body for endogenous synthesis to occur.

The nutritional supplement may be provided in any form known in the art, including a powder, a suspension, a paste, a pudding, a solid, a liquid, a liquid concentrate, or a ready-to-use product. According to certain exemplary embodiment, the nutritional supplement is in a form of a powder.

As used herein, the term "powder" refers to any form of dry material. For powder embodiments of the present invention, such powders are typically in the form of flowable or substantially flowable particulate compositions or at least particulate compositions that can be easily scooped and measured with a spoon or similar other device, wherein the compositions can easily be reconstituted by the intended user with a suitable aqueous fluid, typically water, to form a liquid nutritional formula for immediate oral use. In this context, "immediate" use generally means within about 48 hours, typically within about 24 hours, most typically right after reconstitution. These powder embodiments include spray dried, agglomerated, dry mixed or other known or otherwise effective particulate form.

The quantity of a nutritional powder required to produce a volume suitable for one serving can vary. The number of servings per day can be selected to accommodate the preference of the adolescent. According to certain exemplary embodiments, the quantity of an individual serving is 55-70 g powder. According to these exemplary embodiments, there are two servings per day. One powder serving of the nutritional supplement of the invention can be reconstituted in variable volumes of liquid or other excipients. According to certain exemplary embodiments, one powder serving is dissolved in 200 ml of liquid. According certain embodiments, the liquid is water. According to other embodiments, the liquid is a beverage other than water.

The nutritional supplement of the present invention may be packaged and sealed in single unit dosage forms or in multi-use containers. When in powder form the sealed package can be stored under ambient conditions. Single dosage form is, in one embodiment, a package comprising powder in an amount for one serving to be dissolved in an excipient, typically water or another beverage. In another embodiment a single dosage form is a ready-to-use formula containing one serving of the nutritional supplement. For multi-use containers, the package can be opened and then covered for repeated use by the ultimate user, provided that the covered package is then stored under ambient conditions (e.g., avoid extreme temperatures) and the contents used within about one month or so.

According to some embodiments, the nutritional supplement of the invention is administered by two oral supplement servings per day.

According to yet another aspect, the present invention provides a method for improving the growth of a pre-pubertal human adolescent, comprising administering a nutritional supplement to a pre-pubertal human adolescent having a short stature compared to the norm, wherein the nutritional supplement has per 100 g powder a total caloric content of from about 400 kcal to about 600 kcal comprising per 100 g powder a micronutrient combination comprising calcium in an amount of from about 250 mg to about 650 mg; vitamin C in an amount of from about 15 mg to about 50 mg; zinc in an amount of from about 5.0 mg to about 10 mg; iron in an amount of from about 4.6 mg to about 10 mg; vitamin A in an amount of from about 350 µg to about 400 µg; and vitamin D in an amount of from about 2 µg to about 10 µg, thereby improving the growth of the pre-pubertal human adolescent.

According to certain exemplary embodiments, the term "short stature compared to the norm" refers to a pre-pubertal adolescent subject height below the $10^{th}$ percentile. According to additional embodiments, the subject weight is also below the $10^{th}$ percentile.

According to certain embodiments, the pre-pubertal adolescent subject age is more than 10 years. According to other embodiments the pre-pubertal adolescent subject is healthy. According to yet additional embodiments, the pre-pubertal adolescent subject has normal levels of growth hormone.

According to other embodiments, the method is for enhancing the growth rate of said subject. According to these embodiments, the growth rate in enhanced by additional 0.5-3.0 cm per year relative to the expected growth rate.

The enhancement of the growth rate during time can be constant or variable. It is to be explicitly understood that enhancement of a growth rate includes catch up growth. As used herein, the term "catch up growth" refers to height growth velocity above the normal statistical limits for age and/or maturity during a defined period of time, after a transient period of growth inhibition.

According to additional embodiments, the method is for elevating the final stature measure of said subject relative to the expected measure. According to these embodiments, the final stature measure is elevated by 0.5 cm to 5 cm.

According to yet additional embodiments, the method is for maintaining the growth rate of said subject. According to these embodiments, the nutritional supplement of the invention provides for a growth rate that is similar to the growth rate of a healthy subject of the same gender and age.

According to certain embodiments, the nutritional supplement of the invention is administered at an amount of at least 1 g/kg BW at base-line/day. According to other embodiments, the supplement is administered at an amount of between 1.25 to 5.5 g/kg BW at base-line/day.

There is no significance to the number of portions of the nutritional supplement consumed as long as the minimal total effective amount is consumed. According to some embodiments, the nutritional supplement is administered twice a day. According to certain exemplary embodiments, the nutritional supplement is administered once a day.

According to certain exemplary embodiments, the nutritional supplement is administered once daily for a duration of at least 6 months. According to other embodiments, the nutritional supplement is administered once daily for a duration of at least 7 month, 8 months, 9 months, 10 months, 11 months or 12 months. Each possibility represents a separate embodiment of the present invention. According to certain exemplary embodiments, the nutritional supplement is administered daily for duration of at least 12 months.

According to certain embodiments, the nutritional supplement of the invention is for use in improving the growth of pre-pubertal adolescent subject. According to some embodiments, the age of the subject is more than 10. According to some embodiments, the subject is a male at the age of more than 11. According to some embodiments, the subject is a male subject at the age of more than 13. According to some embodiments, the subject is a female subject at the age of more than 10. According to some embodiments, the subject is a female subject at the age of more than 12. According to other embodiments, the human subject is healthy. According to other embodiments, the human subject has normal levels of growth hormone.

According to other embodiments, the nutritional supplement is for use in the growth rate of said subject. According to these embodiments, the growth rate is enhanced by additional 0.5-3.0 cm per year relative to the expected growth rate.

According to other embodiments, the nutritional supplement is for use in elevating the final stature measure of said subject relative to the expected measure. According to these embodiments, the final stature measure is elevated by 0.5 cm to 5 cm.

According to other embodiments, the nutritional supplement is for use in maintaining the growth rate of said subject.

According to exemplary embodiments, the method comprising administering to a pre-pubertal male adolescent a nutritional supplement comprising per 100 g powder a total caloric content of 440 kcal, comprising per 100 g powder a micronutrient combination comprising calcium in an amount of about 415 mg; vitamin C in an amount of about 23 mg; zinc in an amount of about 6.1 mg; iron in an amount about 4.6 mg; vitamin A in an amount of about 385 µg; and vitamin D in an amount of 2.3 µg.

According to additional exemplary embodiments, the method comprising administering to a pre-pubertal male adolescent a nutritional supplement comprising per 100 g powder a total caloric content of 440 kcal, comprising per 100 g powder a micronutrient combination comprising calcium in an amount of about 415 mg; vitamin C in an amount of about 23 mg; zinc in an amount of about 6.1 mg; iron in an amount about 4.6 mg; vitamin A in an amount of about 385 µg; and vitamin D in an amount of 2.3 µg, wherein the nutritional supplement is administered at an amount of 130 g/day.

According to additional exemplary embodiments, the method comprising administering to a pre-pubertal male adolescent a nutritional supplement comprising per 100 g powder a total caloric content of 440 kcal, comprising per 100 g powder a micronutrient combination comprising calcium in an amount of about 415 mg; vitamin C in an amount of about 23 mg; zinc in an amount of about 6.1 mg; iron in an amount about 4.6 mg; vitamin A in an amount of about 385 µg; and vitamin D in an amount of 2.3 µg, wherein the nutritional supplement is administered at an amount of 130 g/day, and wherein the male is more than 11 years old.

According to additional exemplary embodiments, the method comprising administering to a pre-pubertal male adolescent a nutritional supplement comprising per 100 g powder a total caloric content of 440 kcal, comprising per 100 g powder a micronutrient combination comprising calcium in an amount of about 415 mg; vitamin C in an amount of about 23 mg; zinc in an amount of about 6.1 mg; iron in an amount about 4.6 mg; vitamin A in an amount of about 385 µg; and vitamin D in an amount of 2.3 µg, wherein the nutritional supplement comprises carbohydrate content of about 49 g/100 g powder; total fat content of about 14.7 g/100 g powder; and protein content of about 27.7 g/100 g powder, and wherein the male is more than 11 years old.

According to exemplary embodiments, the method comprising administering to a pre-pubertal female adolescent a nutritional supplement comprising per 100 g powder a total caloric content of 440 kcal, comprising per 100 g powder a micronutrient combination comprising calcium in an amount of about 446 mg; vitamin C in an amount of about 27 mg; zinc in an amount of about 7.1 mg; iron in an amount about 6.2 mg; vitamin A in an amount of about 357 µg; and vitamin D in an amount of 2.7 µg.

According to exemplary embodiments, the method comprising administering to a pre-pubertal female adolescent a nutritional supplement comprising per 100 g powder a total caloric content of 440 kcal, comprising per 100 g powder a micronutrient combination comprising calcium in an amount of about 446 mg; vitamin C in an amount of about 27 mg; zinc in an amount of about 7.1 mg; iron in an amount about 6.2 mg; vitamin A in an amount of about 357 µg; and vitamin D in an amount of 2.7 µg, wherein the pre-pubertal human female is more than 10 years old.

According to exemplary embodiments, the method comprising administering to a pre-pubertal female adolescent a nutritional supplement comprising per 100 g powder a total caloric content of 440 kcal, comprising per 100 g powder a micronutrient combination comprising calcium in an amount of about 446 mg; vitamin C in an amount of about 27 mg; zinc in an amount of about 7.1 mg; iron in an amount about 6.2 mg; vitamin A in an amount of about 357 µg; and vitamin D in an amount of 2.7 µg, wherein the nutritional supplement further comprises carbohydrate content of about 49 g/100 g powder; total fat content of about 14.7 g/100 g powder; and protein content of about 27.7 g/100 g powder, and wherein the pre-pubertal human female is more than 10 years old.

The following examples are presented in order to more fully illustrate some embodiments of the invention. They should, in no way be construed, however, as limiting the broad scope of the invention. One skilled in the art can readily devise many variations and modifications of the principles disclosed herein without departing from the scope of the invention.

EXAMPLES

Example 1: Exemplary Formulation of the Nutritional Supplement

An exemplary formula of the nutritional supplement for pre-pubertal male adolescents is presented in Table 1 hereinbelow.

TABLE 1

Exemplary Nutritional Supplement for pre-pubertal male adolescents

|  | Amount per day 130 g | Amount per 100 g |
|---|---|---|
| Calories | 570 kcal | 440 kcal |
| Total carbohydrate | 64 g | 49 g |
| Total fat | 19 g | 14.7 g |
| Saturated fat | 2.4 g | 1.9 g |
| Protein | 36 g | 27.7 g |

TABLE 1-continued

Exemplary Nutritional Supplement for pre-pubertal male adolescents

| | | Amount per day 130 g | Amount per 100 g |
|---|---|---|---|
| | Sodium | 414 mg | 319 mg |
| | Potassium | 773 mg | 597 mg |
| | Phosphorus | 420 mg | 324 mg |
| | Calcium | 539 mg | 415 mg |
| | Vitamin D | 3 μg | 2.3 μg |
| | Iron | 6 mg | 4.6 mg |
| | Vitamin C | 30 mg | 23 mg |
| | Vitamin A | 500 μg | 385 μg |
| | Zinc | 8 mg | 6.1 mg |
| | Nutritional fibers | 2.1 g | 1.6 g |
| Amino acid | Arginine | 1 g | 0.77 g |
| composition | Lysine | 3.3 g | 2.5 g |
| of total | Tyrosine | 1.2 g | 0.9 g |
| protein | Leucine | 3.8 g | 2.9 g |

An exemplary formula of the nutritional supplement for pre-pubertal female adolescents is presented in table 2 hereinbelow.

TABLE 2

Exemplary Nutritional Supplement for pre-pubertal female adolescents

| | | Amount per day 113 g (in 2 servings) | Amount per 100 g |
|---|---|---|---|
| | Calories | 490 kcal | 440 kcal |
| | Total carbohydrate | 55 g | 49 g |
| | Total fat | 16.5 g | 14.7 g |
| | Saturated fat | 2 g | 1.8 g |
| | Protein | 31 g | 27.7 g |
| | Sodium | 387 mg | 345 mg |
| | Potassium | 710 mg | 634 mg |
| | Phosphorus | 388 mg | 346 mg |
| | Calcium | 500 mg | 446 mg |
| | Vitamin D | 3 μg | 2.7 μg |
| | Iron | 7 mg | 6.2 mg |
| | Vitamin C | 30 mg | 27 mg |
| | Vitamin A | 400 μg | 357 μg |
| | Zinc | 8 mg | 7.1 mg |
| | Nutritional fibers | 2.1 g | 1.9 g |
| Amino acid | Arginine | 0.9 g | 0.8 g |
| composition | Lysine | 2.86 g | 2.5 g |
| of total | Tyrosine | 1 g | 0.9 g |
| protein | Leucine | 3.3 g | 2.9 g |

Example 2: Clinical Study: Effect of the Nutritional Composition on Linear Growth and Weight Gain Material and Methods A clinical study is designed for assessing the effect of the nutritional supplement of the invention on linear growth and weight gain of short and lean pre-pubertal adolescents. The study is a 12-month double blind randomized controlled study (RCT). The study is conducted at the Institute for Endocrinology Schneider Children's Medical Center of Israel. Written informed consent from parents is sought prior to enrolment to the study.

Study Population

Eligible patients are healthy short and lean pre-pubertal adolescents who are referred to the clinic for growth assessment.

Inclusion criteria for boys: age: ≥11 years old; pre-pubertal at Tanner stage 1 (gonadarche)(testicular volume<4 ml); height and weight≤10$^{th}$ percentile for age and gender; Height-SDS≥-2.5 SDS; BMI-SDS>-2 SDS; low proportion between weight and height.

Inclusion criteria for girls: age: ≥10 years old; pre-pubertal at Tanner stage 1 (gonadarche) (Breast at Tanner stage 1); height and weight<10th percentile for age and gender; Height-SDS>-2.5 SDS; BMI-SDS>-2 SDS; low proportion between weight and height.

Exclusion criteria include:

1. Diagnosis of GH Deficiency or treatment with GH
2. Any known chronic disease or dismorphic syndrome including: bone diseases, organic brain diseases, neurological disease, past or current malignancy, chronic cardiac, renal or pulmonary problems
3. Any known gastrointestinal disease including malabsorption
4. Any known organic reason for growth retardation
5. Any chronic treatment with medication that might affect appetite, weight or growth (for example SSRI's).

Methods:

Randomization & Blinding:

Participants are randomly assigned either to the intervention group or the placebo control group. Randomization for the two study groups are made in a ratio of 1:1. Both participants and study team are blinded to the type of treatment that each patient receives during the study.

Treatment:

Participants in the intervention groups are treated with a nutritional gender specified supplementation formula (Powder added to water), containing about 25% of recommended DRI for Calories, high protein (25% of calories) and multi vitamin and mineral [25%-100% of DRI for recommended daily allowance (RDA) or adequate intake (AI)]. Participants in the control group are treated with a placebo low caloric formula (Powder added to water), without added vitamins and minerals.

All the participants are instructed to use 1 sachet, containing 5-6 spoons of powder, mixed with 200-300 ml of water per day. The total daily amount of formula is calculated based on target body weight and nutrition needs for 50th percentile for age and gender.

Treatment Duration:

The study continues for 6 months of intervention versus active placebo, with additional 6 months (an extension period), in which participants at both groups, the intervention and the placebo, are offered to continue their participation in the study with the study supplement.

Study Schedule:

Follow up visits are taken place at 0, 3, 6, 9, and 12 months and include:

1. Demographic data, medical history and growth data (month 0):

Demographic parameters, including birth date, gender, birth weight and length for gestational age, medical history and growth data, parents' and sibling's weight and height are documented from patient's file.

2. Nutritional assessment:

Participant's parents are asked to complete the following (months 0, 3, 6, 9, 12,):

A. 3-day food diary—After receiving a short training by a dietician, participant's parents are asked to record, in as much detail as possible, all food and beverages consumed over a 3-day period. They are allowed to describe their portion size in other measures, such as weights or household units.

B. Daily amount documentation table—The participant's parents are asked to document, at the end of the day, the amount of the formula that left in the jar and calculate the amount that the child has eat/drank during the day.

This chart is for assessment of participant's compliance to consume the daily dose of the formula.

3. Anthropometric assessment (months 0, 3, 6, 9, 12,):

A. Height without shoes

B. Weight with light cloths and without shoes

C. Body mass index (BMI) is calculated from children's weight and height and age and gender specific BMI SDS is calculated D. Body composition—using the method of bioelectrical impedance analysis (BIA), (TANITA BC-420MA P), after night fast.

E. Body composition—using the BOD POD composition tracking system, which uses whole body densitometry to determine body composition. The BOD POD is an air displacement plethysmography system using whole body densitometric principles to determine body composition (Fat and fat-free mass) in adults and children. This technique relies on a mass measurement from a highly accurate scale and a volume measurement from the BOD POD chamber. Once the body density is determined the BOD POD measures or predicts thoracic gas volume, it is uses known densitometric equations to calculate percent fat and fat free mass. The accuracy of the BOD POD has been shown to be very high compared to reference techniques and is considered the practical gold standard for body composition assessment. The BOD POD assessment is safe and non-invasive. During the assessment the patient has to get into the BOD POD chamber for two minutes with a swimsuit (BOD POD Operator's manual, 2004). Measurement of body composition using BOD POD is done on a representative sample of 40 participants, 20 from each group (visits 0, 6, 12).

4. Puberty assessment (months 0, 6, and 12):

Tanner stage will be assessed by an endocrinologist.

5. Laboratory parameters (months 0, 6, and 12):

Fasting blood tests is performed to assess the following:

A. For immediate analysis: Hemoglobin, glucose, lipids profile (TG, HDL, LDL, Total cholesterol), total proteins, albumin, and liver function, basal levels of LH, FSH and E2.

B. For future analysis, serum is kept frozen: ferritin, iron, B12, folic acid, insulin, thyroid function (month 0 only), IGF-1, IGFBP1&3, Leptin, Gherlin, GLP-1 and additional growth markers, which will be revealed in the future.

6. Formula dispensing and accountability—(visits 1-5)

7. Formula taste test.—(visits 2-5)

8. Pediatric Quality Of Life Inventory (PedsQL) 4.0 (Varni et al, 2001)—The PesdQL is a generic health-related quality of life measure developed for children and adolescents. Scores are calculated for each of the four core subscales (physical functioning, eight items; emotional functioning, five items; social functioning, five items; and school functioning, five items, as well as the two broad domains: physical and psychosocial functioning), and total score. The scales are standardized, ranging from 0 to 100, with higher scores representing better quality of life. The PedsQL has been shown to be reliable and valid, with internal consistency reliability coefficients approaching or exceeding 0.70. The Hebrew version of the PedsQL 4.0, had been linguistically validated (The PedsQL Organization).

Participants are asked to complete the PedsQL at study visits number 1,3 & 5 (month 0, 6, and 12).

9. Rosenberg Self-Esteem Scale (Rosenberg, 1965)—The Rosenberg self-esteem scale measures state self-esteem by asking the respondents to reflect their current feelings. It is a ten-item Likert-type scale with items answered on a four-point scale, from "strongly agree" to "strongly disagree". Five of the items have positively worded statements and five have negatively worded ones. The Hebrew version of Rosenberg self-esteem scale is considered a reliable and valid quantitative tool for self-esteem assessment. (Hobfoll & Walfisch, 1984). (visits 1, 3, and 5).

10. Sleep Assessment

Several studies reported a relationship between sleep physiology and growth hormone secretion (Takahashi et al., 1968; Sasin et al., 1969; Finkelstein et al., 1971, Van Cauter et al 1998). However, several later studies did not find association between sleep duration and growth variables in children and adolescents (Jenni et al 2007, Gulliford et al 1990, Knutson et al 2005). More studies are needed to establish the relationships between sleep duration and growth in children.

This study explores whether sleep duration can affect growth and serve as a mediating factor between nutrition and growth.

Patients are asked to complete sleep assessment questionnaire (Werner et al, 2008) at study visits number 1, 3, and 5 (month 0, 6, and 12).

11. Physical activity questionnaire (Tao et al, 2007)

Two questions about PA (with proved reliability) are used to evaluate physical activity level: (a) how many times in a normal week respondents engaged in vigorous physical activities making you sweat and breathe hard (e.g. running, playing ball, fast bicycling, not including sport class) or (b) in moderate physical activities making you not sweat or breathe hard (e.g. walking, bicycling at normal tempo, playing Taiji, jumping ropes etc., not including sport class) for at least 20 min. Responses are used to calculate a PA score based on frequency of participation in 'vigorous' (7.5 metabolic equivalents) and 'moderate' (4 metabolic equivalents).

$$PA\ score = frequency \times 20 \times 4(moderate) + frequency \times 20 \times 7.5(vigorous)$$

According to PA scores calculated by the above formation, intensity of PA is categorized as 'very low' (PA score<200; no reported PA or one session per week); 'low' (200≥PA score<400; two to three sessions of moderate or vigorous PA per week); 'moderate' (400≥PA score<560; e.g. five sessions per week of moderate-intensity PA or three sessions per week of vigorous PA); or 'high' (PA score≥560; e.g. daily moderate intensity PA or four or more sessions of vigorous PA).

Patients are asked to complete Physical activity questionnaire (Tao et al, 2007) at study visits number 1, 3, and 5.

12. Three follow up phone call visits take place at: A. one-two weeks after visit 1, B. between visit 2 and visit 3 (between month 3 and month 6) and C. between visit 3 to visit 4 (between month 6 to month 9).

| Flow chart: | | | | | |
|---|---|---|---|---|---|
| Visit | 1 | 2 | 3 | 4 | 5 |
| Month | 0 | 3 | 6 | 9 | 12 |
| Informed consent | X | | | | |
| Check of Incl/Excl | X | | | | |
| Demographics | X | | | | |
| Medical history | X | | | | |
| Concomitant illness & medications | X | X | X | X | X |
| Height & weight | X | X | X | X | X |
| Body composition/TANITA | X | X | X | X | X |
| Body composition/BOD-POD (n = 40) | X | | X | | X |
| Tanner stage | X | | X | | X |
| AE/SAE recording | | X | X | X | X |
| Randomization | X | | | | |
| Laboratory assessment | X | | X | | X |
| 3-days food diary | X | X | X | X | X |
| QOLQ Questionnaire | X | | X | | X |
| Self esteem Questionnare | X | | X | | X |
| Sleep assessment Questionnaire | X | | X | | X |
| Formula dispensing & accountability | X Dispensing only | X | X | X | X Accountability only |
| Physical activity questionnaire | X | | X | | X |
| Formula taste test | | X | X | X | X |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method for improving the growth of a pre-pubertal human adolescent not suffering from malabsorption, comprising administering a nutritional supplement to a pre-pubertal human adolescent having a short stature compared to the norm, wherein the nutritional supplement has per 100 g powder a total caloric content of from about 400 kcal to about 600 kcal, said nutritional supplement comprises per 100 g powder a micronutrient combination comprising calcium in an amount of from about 250 mg to about 650 mg; vitamin C in an amount of from about 15 mg to about 50 mg; zinc in an amount of from about 5.0 mg to about 10 mg; iron in an amount of from about 4.6 mg to about 10 mg; vitamin A in an amount of from about 350 μg to about 400 μg; and vitamin D in an amount of from about 2 μg to about 10 μg, thereby improving the growth of the pre-pubertal human adolescent, wherein when said pre-pubertal human adolescent is a male the nutritional supplement comprises iron at an amount of below 5 mg per 100 g powder and wherein when said pre-pubertal human adolescent is a female the nutritional supplement comprises iron at an amount of above 5 mg per 100 g powder and further wherein the pre-pubertal human male is more than 11 years old and the pre-pubertal human female is more than 10 years old.

2. The method of claim 1, wherein the pre-pubertal adolescent height is below the 10th percentile.

3. The method of claim 1, said method results in enhancing the linear growth rate of the pre-pubertal adolescent.

4. The method of claim 1, said method results in elevating the final stature measure of said subject relative to the expected measure.

5. The method of claim 1, said method is for maintaining the growth rate of the pre-pubertal adolescent.

6. The method of claim 1, wherein the nutritional supplement is for pre-pubertal human male adolescent, said nutritional supplement comprises per 100 g powder a total caloric content of 440 kcal, comprising per 100 g powder a micronutrient combination comprising calcium in an amount of about 415 mg; vitamin C in an amount of about 23 mg; zinc in an amount of about 6.1 mg; iron in an amount about 4.6 mg; vitamin A in an amount of about 385 μg; and vitamin D in an amount of 2.3 μg.

7. The method of claim 1, wherein the nutritional supplement is for pre-pubertal human female adolescent, said nutritional supplement comprises per 100 g powder a total caloric content of 440 kcal, comprising per 100 g powder a micronutrient combination comprising calcium in an amount of about 446 mg; vitamin C in an amount of about 27 mg; zinc in an amount of about 7.1 mg; iron in an amount about 6.2 mg; vitamin A in an amount of about 357 μg; and vitamin D in an amount of 2.7 μg.

8. The method of claim 1, the carbohydrate component of the nutritional supplement comprises from 38% to 52% of the total caloric content of the supplement.

9. The method of claim 1, the fat component of the nutritional supplement comprises from 20% to 35% of the total caloric content of the supplement.

10. The method of claim 1, the protein component of the nutritional supplement comprises from 20% to 32% of the total caloric content of the supplement.

* * * * *